United States Patent
Camire et al.

(10) Patent No.: US 10,676,731 B2
(45) Date of Patent: Jun. 9, 2020

(54) COMPOSITIONS AND METHODS FOR MODULATING FACTOR IX FUNCTION

(71) Applicant: The Children's Hospital of Philadelphia, Philadelphia, PA (US)

(72) Inventors: Rodney M. Camire, Sicklerville, NJ (US); Lacramioara Ivanciu, Philadelphia, PA (US); Valder R. Arruda, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 289 days.

(21) Appl. No.: 15/504,874

(22) PCT Filed: Aug. 19, 2015

(86) PCT No.: PCT/US2015/045858
§ 371 (c)(1),
(2) Date: Feb. 17, 2017

(87) PCT Pub. No.: WO2016/028872
PCT Pub. Date: Feb. 25, 2016

(65) Prior Publication Data
US 2019/0024071 A1    Jan. 24, 2019

Related U.S. Application Data

(60) Provisional application No. 62/039,178, filed on Aug. 19, 2014.

(51) Int. Cl.
*A61K 49/04* (2006.01)
*C12N 9/64* (2006.01)
*C07K 14/745* (2006.01)
*A61K 38/00* (2006.01)

(52) U.S. Cl.
CPC ............ *C12N 9/644* (2013.01); *C07K 14/745* (2013.01); *C12Y 304/21022* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,133,256 A | 10/2000 | Scarborough et al. | |
| 6,262,047 B1 | 7/2001 | Zhu et al. | |
| 6,369,080 B2 | 4/2002 | Zhu et al. | |
| 6,562,598 B1 | 5/2003 | Himmelspach et al. | |
| 6,573,071 B1 | 6/2003 | Himmelspach et al. | |
| 6,905,846 B2 | 6/2005 | Himmelspach et al. | |
| 6,958,322 B1 | 10/2005 | Himmelspach et al. | |
| 7,220,569 B2 | 5/2007 | Himmelspach et al. | |
| 8,153,590 B2 | 4/2012 | Lu et al. | |
| 8,268,783 B2 | 9/2012 | Sinha et al. | |
| 8,383,386 B2 | 2/2013 | Camire | |
| 8,455,439 B2 | 6/2013 | Lu et al. | |
| 9,371,522 B2 | 6/2016 | Camire | |
| 9,410,137 B2 | 8/2016 | Camire | |
| 10,106,786 B2 | 10/2018 | Camire | |
| 2003/0138914 A1 | 7/2003 | Himmelspach et al. | |
| 2003/0181381 A1 | 9/2003 | Himmelspach et al. | |
| 2008/0318276 A1 | 12/2008 | Persson et al. | |
| 2009/0042787 A1 | 2/2009 | Metzner et al. | |
| 2009/0098119 A1 | 4/2009 | Lu et al. | |
| 2009/0175931 A1 | 7/2009 | Camire et al. | |
| 2010/0255000 A1 | 10/2010 | Sinha et al. | |
| 2010/0297257 A1 | 11/2010 | Smith et al. | |
| 2011/0015128 A1 | 1/2011 | Sinha et al. | |
| 2014/0186327 A1 | 7/2014 | Schellenberger et al. | |
| 2016/0362673 A1 | 12/2016 | Camire et al. | |

FOREIGN PATENT DOCUMENTS

| | | |
|---|---|---|
| EP | 1728798 A1 | 12/2006 |
| FR | 2841904 A1 | 1/2004 |
| GB | 2485590 A | 5/2012 |
| WO | 1998/038317 A1 | 9/1998 |
| WO | 1998/038318 A1 | 9/1998 |
| WO | 00/15250 A2 | 3/2000 |
| WO | 2001/070763 A1 | 9/2001 |
| WO | 2004/005347 A1 | 1/2004 |
| WO | 2007/059513 A2 | 5/2007 |
| WO | 2012/117203 A1 | 9/2012 |
| WO | 2013/049804 A1 | 4/2013 |
| WO | 2013/123248 A1 | 8/2013 |
| WO | 2014/108632 A1 | 7/2014 |
| WO | 2014/118677 A1 | 8/2014 |

OTHER PUBLICATIONS

Schuettrumpf (Blood, Mar. 2005, vol. 105, No. 6, pp. 2316-2323).*
Milanov P. et al., "Engineered factor IX variants bypass FVIII and correct hemophilia A phenotype in mice" Blood (2012) 119(2):602-611.
Smith, S.B., "The Molecular Mechanism of Factor IX Activation by Factor IXa" Vanderbilt University (2009) available at https://etd.library.vanderbilt.edu/available/etd-03272009-134726/unrestricted/SBS(Thesis).pdf.
Sun, T., et al. "Vitamin K epoxide reductase significantly improves carboxylation in a cell line overexpressing factor X." Blood (2005) 106(12):3811-3815.
Camire, R., et al. "Enhanced gamma-carboxylation of recombinant factor X using a chimeric construct containing the prothromcin propeptide." Biochemistry (2000) 39(46): 14322-14329.
Camire, R. "Prothrombinase assembly and S1 site occupation restore the catalytic activity of FXa impaired by mutation at the sodium-binding site." Journal of Biological Chemistry (2002) 277(40):37863-37870.

(Continued)

*Primary Examiner* — Hope A Robinson
(74) *Attorney, Agent, or Firm* — Robert C. Netter, Jr.; Dann, Dorfman, Herrell & Skillman

(57) ABSTRACT

Factor IX/IXa variants and methods of use thereof are disclosed.

6 Claims, 13 Drawing Sheets

Specification includes a Sequence Listing.

(56) References Cited

OTHER PUBLICATIONS

Hedstrom, L., et al. "Hydrophobic interactions control zymogen activation in the trypsin family of serine proteases." Biochemistry (1996) 35(14): 4515-4523.
Toso, R., et al. "Factor VII mutant V154G models a zymogen-like form of factor VIIa." The Biochemical Journal (2003) 369(3):563-571.
Toso, R., et al. "Factor VII variants as tools to study Factor VIIa salt bridge formation." Database Biosis. Biosciences, Information Service, Philadelphia, PA & Blood (2001) 98(11):526a [Abstract].
Toso, R., et al. "Alteration of the factor X zymogen to protease transition provides evidence for allosteric linkage between the S1 and FVa binding sites." Blood (2005) 106(11):Abstract 30.
Toso, R., et al. "The conformational switch from the factor X zymogen to protease state mediates exosite expression and prothrombinase assembly." Journal of Biological Chemistry (2008) 283(17):18627-18635.
Wells, J.A., "Additivity of Mutational effects in Proteins" (1990) Biochemistry 29(37):8509-8517.
Guo, H.H., et al., "Protein Tolerance to random Amino Acid Change," PNAS (2004) 101:9205-9210.
Hult, K., "Engineered Enzymes for Improved Organic Synthesis," Curr. Opin. Biotech. (2003) 14:395-400.
Stanberg, L., et al., "Variants of Tissue-type Plasminogen Activator with Substantially Enhanced Response and Selectivity toward Fibrin Co-factors," J. Biol. Chem. (1995) 270(40):23444-23449.

Bianchini, E.P., et al., "Mapping of the Catalytic Groove Preferences of Factor Xa Reveals an Inadequate Selectivity for its Macromolecular Substrates" J. Biol. Chem. (2002) 277(23):20527-20534.
Rudinger, J., "Characteristics of the Amino Acids as Components of a Peptide Hormone Sequence" in Peptide Hormones, J.A. Parsons (ed.), Univ. Park Press, Baltimore, pp. 1-7 (1976).
Friedrich, R., et al. "Staphylocoagulase is a prototype for the mechanism of cofactor induced zymogen activation." Nature (2003) 425: 535-539.
Rudolph, A.E., et al., "Expression, Purification, and Characterization of Recombinant Human Factor X," Protein Expressions Purif. (1997) 10:373-378.
Ngo, J.T., "Computational Complexity, Protein Structure Prediction, and the Levinthal Paradox" in Peptide Hormones, J.A. Parsons (ed.), Univ. Park Press, Baltimore, pp. 491-495 (1976).
Ivanciu, L., et al. "Correction of the Coagulation Defect in Hemophilia using a Factor Xa Variant with Novel Engineered Protease Function," Nat. Biotechnol. (2011) 29(11):1028-1033.
Bunce, M.W., "Zymogen-like Factor Xa Variants Restore Thrombin Generation and Effectively Bypass the Intrinsic Pathway in Vitro," Blood (2011) 117(1):290-298.
Al-Tamimi, M., et al. "Coagulation-induced shedding of platelet glycoprotein VI mediated by factor Xa" Blood (2011) 117(14):3912-20.
Thalji, N.K., et al., "Zymogen-Like FXa is an Effective Pro-Hemostatic to Reverse the Anticoagulant Effects of Direct FXa Inhibitors" Blood (2013) 122(21):2383.
Brandstetter, et al., "X-ray structure of clotting factor IXa: Active site and module structure related to Xase activity and hemophilia B" Proc. Natl. Acad. Sci. (1995) 92:9796-9800.

* cited by examiner

```
  1 MQRVNMIMAE SPGLITICLL GYLLSAECTV FLDHENANKI LNRPKRYNSG KLEEFVQGNL
 61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL T
```

Figure 2A

YNSG KLEEFVQGNL ERECMEEKCS FEEAREVFEN TERTTEFWKQ YVDGDQCESN
PCLNGGSCKD DINSYECWCP FGFEGKNCEL DVTCNIKNGR CEQFCKNSAD
NKVVCSCTEG YRLAENQKSC EPAVPFPCGR VSVSQTSKLT R

Light Chain

AETVFPDVD YVNSTEAETI LDNITQSTQS FNDFTRVVGG EDAKPGQFPW
QVVLNGKVDA FCGGSIVNEK WIVTAAHCVE TGVKITVVAG EHNIEETEHT
EQKRNVIRII PHHNYNAAIN KYNHDIALLE LDEPLVLNSY VTPICIADKE
YTNIFLKFGS GYVSGWGRVF HKGRSALVLQ YLRVPLVDRA TCLRSTKFTI
YNNMFCAGFH EGGRDSCQGD SGGPHVTEVE GTSFLTGIIS WGEECAMKGK
YGIYTKVSRY VNWIKEKTKL T

Heavy Chain

Figure 2B

YNSG KLEEFVQGNL ERECMEEKCS FEEAREVFEN TERTTEFWKQ YVDGDQCESN
PCLNGGSCKD DINSYECWCP FGFEGKNCEL DVTCNIKNGR CEQFCKNSAD
NKVVCSCTEG YRLAENQKSC EPAVPFPCGR VSVSQTSKLT R

Light Chain

VVGG EDAKPGQFPW QVVLNGKVDA FCGGSIVNEK WIVTAAHCVE TGVKITVVAG
EHNIEETEHT EQKRNVIRII PHHNYNAAIN KYNHDIALLE LDEPLVLNSY
VTPICIADKE YTNIFLKFGS GYVSGWGRVF HKGRSALVLQ YLRVPLVDRA
TCLRSTKFTI YNNMFCAGFH EGGRDSCQGD SGGPHVTEVE GTSFLTGIIS
WGEECAMKGK YGIYTKVSRY VNWIKEKTKL T

Heavy Chain

Figure 2C

```
a tgcagcgcgt gaacatgatc atggcagaat
caccaggcct catcaccatc tgccttttag gatatctact cagtgctgaa tgtacagttt
ttcttgatca tgaaaacgcc aacaaaattc tgaatcggcc aaagaggtat aattcaggta
aattggaaga gtttgttcaa gggaaccttg agagagaatg tatggaagaa aagtgtagtt
ttgaagaagc acgagaagtt tttgaaaaca ctgaagaac aactgaattt tggaagcagt
atgttgatgg agatcagtgt gagtccaatc catgtttaaa tggcggcagt tgcaaggatg
acattaattc ctatgaatgt tggtgtccct ttggatttga aggaaagaac tgtgaattag
atgtaacatg taacattaag aatggcagat gcgagcagtt ttgtaaaaat agtgctgata
acaaggtggt ttgctcctgt actgagggat atcgacttgc agaaaaccag aagtcctgtg
aaccagcagt gccatttcca tgtggaagag tttctgtttc acaaacttct aagctcaccc
gtgctgagac tgtttttcct gatgtggact atgtaaattc tactgaagct gaaaccattt
tggataacat cactcaaagc acccaatcat ttaatgactt cactcgggtt gttggtggag
aagatgccaa accaggtcaa ttccttggc aggttgtttt gaatggtaaa gttgatgcat
tctgtggagg ctctatcgtt aatgaaaaat ggattgtaac tgctgcccac tgtgttgaaa
ctggtgttaa aattacagtt gtcgcaggtg aacataatat tgaggagaca gaacatacag
agcaaaagcg aaatgtgatt cgaattattc ctcaccacaa ctacaatgca gctattaata
agtacaacca tgacattgcc cttctggaac tggacgaacc cttagtgcta aacagctacg
ttacacctat ttgcattgct gacaaggaat acacgaacat cttcctcaaa tttggatctg
gctatgtaag tggctgggga agagtcttcc acaagggag atcagcttta gttcttcagt
accttagagt tccacttgtt gaccgagcca catgtcttcg atctacaaag ttcaccatct
ataacaacat gttctgtgct ggcttccatg aaggaggtag agattcatgt caaggagata
gtgggggacc ccatgttact gaagtggaag ggaccagttt cttaactgga attattagct
ggggtgaaga gtgtgcaatg aaaggcaaat atgaatata taccaaggta tcccggtatg
tcaactggat taaggaaaaa acaaagctca cttaa
```

Figure 2D

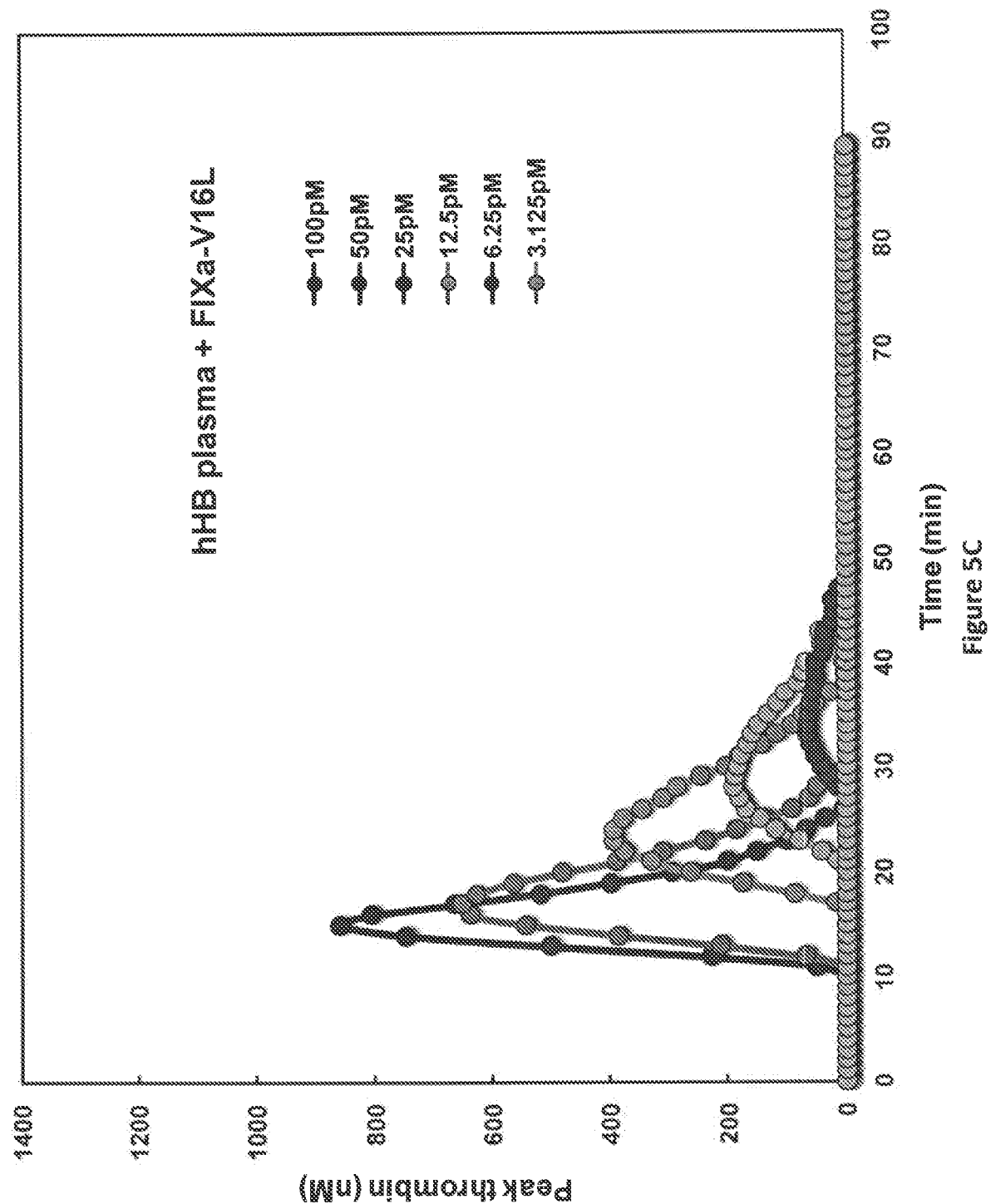

COMPOSITIONS AND METHODS FOR MODULATING FACTOR IX FUNCTION

This application is a § 371 application of PCT/US2015/045858, filed Aug. 19, 2015, which claims priority under 35 U.S.C. § 119(e) to U.S. Provisional Patent Application No. 62/039,178, filed Aug. 19, 2014. The foregoing applications are is incorporated by reference herein.

This invention was made with government support under Grant Numbers R01 HL-074124 awarded by the National Institutes of Health. The government has certain rights in the invention.

FIELD OF THE INVENTION

The present invention relates to the fields of medicine and hematology. More specifically, the invention provides novel Factor IX variants and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

In response to vascular injury such as a cut, coagulation enzymes are activated in a stepwise manner, ultimately resulting in the formation of a blood clot at the site of injury. Thrombin is generated from its inactive precursor prothrombin in the final step of this cascade and subsequently produces the fibrous clot. Activated Factor IX (FIXa) is a key component of this system as it is the serine protease of the intrinsic Xase complex, which also comprises the co-factor activated Factor VIII (FVIIIa). This enzyme, assembled on cells with exposed anionic membranes, rapidly converts Factor X to activated Factor X (FXa). FXa and its co-factor, activated Factor V (FVa), form prothrombinase, the enzyme complex that activates thrombin.

The importance of Factor IX is reflected by the occurrence of the bleeding disorder hemophilia B in individuals carrying mutations in the Factor IX gene. In bleeding disorders such as hemophilia B, a defect or deficiency of Factor IX results in inadequate FXa generation and, therefore, inadequate thrombin formation. Replacement of the missing protein is the mainstay of hemophilia treatment. Although effective, there are several limitations with current protein replacement therapies. For example, current therapies suffer from the short-half life of the proteins administered, thereby requiring multiple intravenous injections at high doses. Therefore, there is an obvious need for clotting factors with improved biological properties.

SUMMARY OF THE INVENTION

In accordance with the present invention, compositions and methods for the modulation of hemostasis in patients in need thereof are provided. More specifically, Factor IX/Factor IXa variants which modulate (e.g., increase) hemostasis are provided. In a particular embodiment, the variant comprises at least one modification of the Val at position 16 and/or the Val at position 17. Nucleic acids encoding the variants of the invention are also disclosed as are methods of use thereof. Such nucleic acid molecules may optionally encode an intracellular cleavage site (e.g., PACE/furin). Another aspect of the invention includes host cells expressing the variant of the invention. Methods for isolating and purifying the variants are also disclosed.

Pharmaceutical compositions comprising the variants of the invention in a carrier are also provided. The invention also includes methods for the treatment of a hemostasis related disorder in a patient in need thereof comprising administration of a therapeutically effective amount of the variant containing pharmaceutical compositions described herein. Such methods have efficacy in the treatment of disorders where a pro-coagulant is needed and include, without limitation, hemophilia, particularly hemophilia B.

BRIEF DESCRIPTION OF THE DRAWINGS

FIG. 2A provides an amino acid sequence of human Pre-Pro-Factor IX (SEQ ID NO: 1). The underlined and bolded residues are positions 16 and 17 in chymotrypsin numbering. FIG. 2B provides an amino acid sequence of the light chain (SEQ ID NO: 2) and heavy chain (SEQ ID NO: 3) of Factor IX. FIG. 2C provides an amino acid sequence of the light chain (SEQ ID NO: 2) and heavy chain (SEQ ID NO: 4) of activated Factor IX (FIXa). FIG. 2D provides a nucleic acid sequence (SEQ ID NO: 5) which encodes human Factor IX preproprotein.

FIGS. 5A, 5B, and 5C provide a timecourse of FIXa thrombin generation for wild-type FIXa, FIXa V17I, and FIXa V16L, respectively.

DETAILED DESCRIPTION OF THE INVENTION

Figure 1:
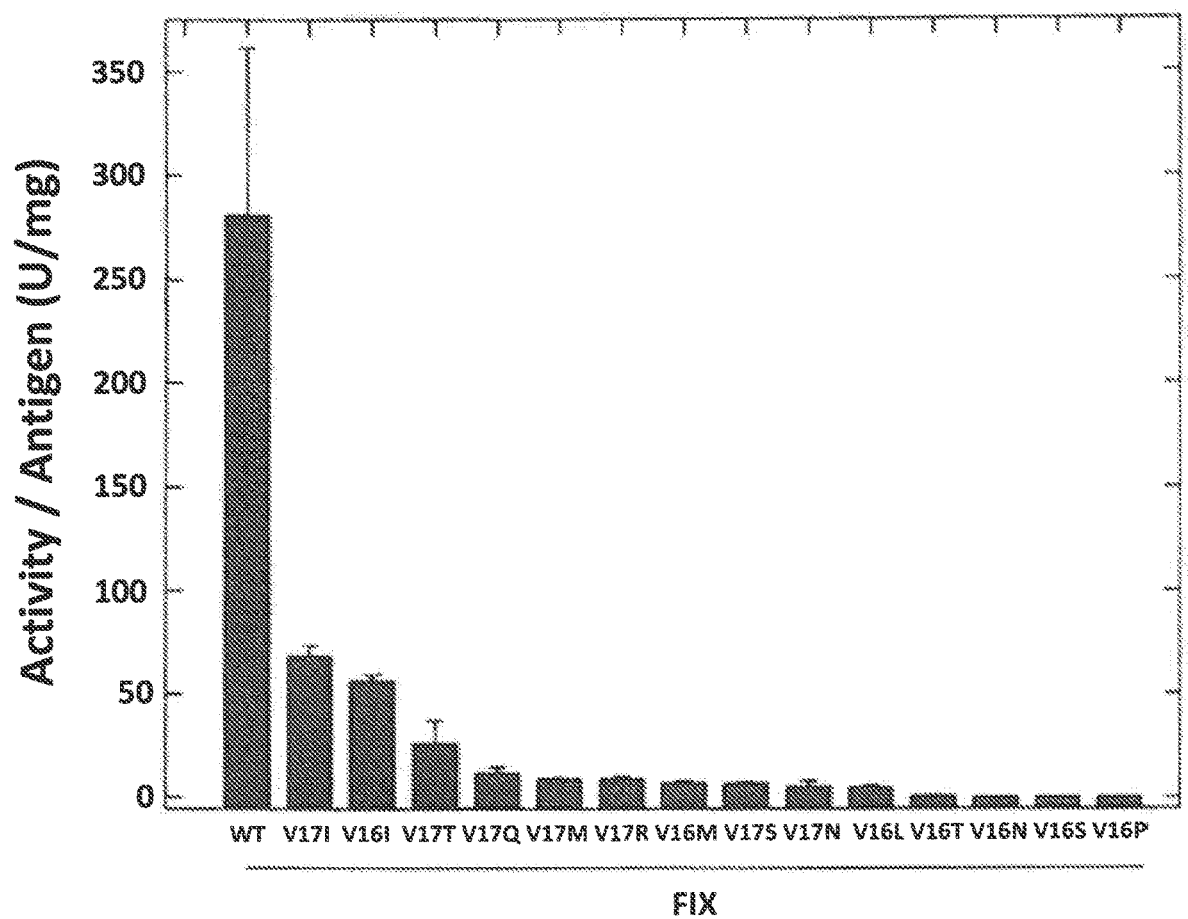
FIG. 1 provides a graph of Factor IX variant specific activity normalized to antigen levels for the indicated Factor IX variants. The values given are the average (±SEM) from three separate experiments.

Herein, novel zymogen-like Factor IX variants are provided. In particular, Factor IX variants comprising a mutation at position 16 and/or 17 (in chymotrypsin numbering) are provided. Without being bound by theory, the mutations in the Factor IX variants alter the normal conformational change required for protease formation. The Factor IX variants of the instant invention have a prolonged biological half-life, e.g., following activation when compared with wild-type FIXa and retain high biologic activity, particularly once incorporated within the intrinsic Xase complex (FIXa-FVIIIa-membranes).

The blood coagulation response is a defense mechanism that has evolved to protect organisms from significant loss of blood following injury. As explained briefly hereinabove, coagulation proceeds through a series of proteolytic reactions, each of which converts an inert zymogen (inactive) in blood to a serine protease (active) product. Thrombin, the final serine protease product of the blood coagulation cascade, activates platelets and cleaves a structural protein (fibrinogen) to generate fibrin, thereby providing a meshwork which physically prevents blood from leaving the vessel. Deviation from this process leads to the pathological state of bleeding. This is particularly true in the case of a defect or deficiency of Factor IX. Such a deficiency in Factor IX activity results in the inherited bleeding disorder hemophilia B. Protein replacement therapy with intravenously delivered plasma-derived or recombinant Factor IX is the standard of care for hemophilia B patients. While this therapy is efficient, this therapy requires frequent (e.g., 2-3 times per week) intravenous administration of large amounts of Factor IX due to the short half-life of the protein. While existing strategies have focused on increasing the half-life of Factor IX, the present invention provides Factor IX variants which have an increased biological half-life in plasma in the activated form compared to wild-type FIXa.

Herein, selective alteration of the Factor IX zymogen to protease transition through mutagenesis has been used to develop zymogen-like Factor IX variants. In a particular embodiment, these novel Factor IX variants lack activity or have minimal activity (e.g., less than about 10%, less than about 5%, or less than about 1% of wild type) in the absence of the cofactor FVIIIa. The mutations of the instant invention enhance the stability of the protease, increase its biologic half-life, and, therefore, reduce the dosage requirements for treatment and/or prevention of bleeding episodes, e.g., via protein replacement therapy and/or gene therapy. With regard to gene therapy, the continuous presence in the blood stream of the zymogen-like Factor IX variants of the instant invention would result in the reduction and/or elimination of the frequency of bleeding events (e.g., spontaneous bleeds). Greater efficacy of the Factor IX variants will translate into lower vector doses to achieve therapeutic benefit.

Factor IX circulates in plasma as an inactive zymogen (57 kDa) at a concentration of approximately 90 nM. Factor IX is initially synthesized in the liver harboring a ~40 amino acid pre-pro-leader sequence which is removed upon secretion of the protein. Upon vascular damage, Factor IX is activated to FIXa following cleavage of two bonds by either the Factor VIIa/tissue factor (TF) complex or Factor XIa—releasing a 35-residue activation peptide. Free FIXa is rapidly eliminated by reactions with circulating serpins, most notably antithrombin III (ATIII).

Activation of Factor IX follows a well-described mechanism. Bond cleavage at a highly conserved site ($R^{15}$-$V^{16}$VGG, in chymotrypsin numbering system) unmasks a new N-terminus ($V^{16}V^{17}$GG) of the heavy chain. After cleavage, the intermediate is in a "zymogen-like state," which rapidly equilibrates to the protease state after the newly generated N-terminus inserts into the activation pocket and forms a salt-bridge with the $Asp^{194}$. This interaction is a defining characteristic of the conversion of zymogen to active enzyme. The zymogen state and the protease state exist in an equilibrium that can be shifted depending on various ligands. Here, the zymogen to protease equilibrium of FIXa is perturbed to yield proteins with zymogen-like properties. Since $Val^{16}$ and $Val^{17}$ are key residues of the zymogen to protease transition, mutations at these positions alter the conversion of Factor IX to FIXa and, thus, negatively impact the binding of certain ligands or inhibitors to the protease domain. The activity of the FIXa variants of the instant invention may be restored through the presence of the cofactor FVIIIa.

The instant invention encompasses variant Factor IX molecules including FIXa variants, Factor IX variants, Factor IX prepropeptide variants, and Factor IX propeptide variants. For simplicity, the variants are generally described throughout the application in the context of FIXa. However, the invention contemplates and encompasses Factor IX, Factor IX prepropeptide, and Factor IX propeptide molecules having the same amino acid substitutions.

The FIXa variants of the instant invention can be from any mammalian species. In a particular embodiment, the FIXa variant is human. Gene ID: 2158 and GenBank Accession Nos. NM_000133.3 and NP_000124.1 provide examples of the amino acid and nucleotide sequences of wild-type human Factor IX preproprotein. FIG. 2A provides SEQ ID NO: 1, which is an example of the amino acid sequence of the human Factor IX preproprotein. The Factor IX prepopetide comprises a signal peptide from amino acids 1-28 and a propeptide sequence from amino acids 29-46. The cleavage of the propeptide yields a protein with a new terminus sequence of Tyr-Asn-Ser. Factor IX is also cleaved by the FVIIa/TF complex or FXIa into a mature two-chain form (light and heavy) at an arginyl-alanine peptide bond to generate the Factor IX zymogen. The two chains are linked via a disulfide bond. FIG. 2B provides SEQ ID NOs: 2 and 3, which are examples of the amino acid sequence of the human Factor IX light and heavy chains, respectively. Factor IX is activated by the cleavage of the 35 amino acid activation peptide at an arginyl-valine peptide bond by the FVIIa/TF complex or FXIa to yield a new amino-terminal sequence of VVGG (SEQ ID NO: 6) for wild-type FIXa heavy chain (SEQ ID NO: 4). FIG. 2C provides SEQ ID NOs: 2 and 4, which are examples of the amino acid sequence of the human FIXa light and heavy chains. Notably, the above proteolytic cleavage events may be imprecise, thereby leading to addition or loss of amino acids (e.g., 1, 2, 3, or more amino acids) at the cleavage sites. FIG. 2D provides a nucleic acid sequence (SEQ ID NO: 5) which encodes human Factor IX preproprotein. Nucleic acid molecules which encode Factor IX and FIXa can be readily determined from the provided amino acid and nucleotide sequences.

In a particular embodiment, the variant of the instant invention has at least 75%, 80%, 85%, 90%, 95%, 97%, 99%, or 100% homology (identity) with SEQ ID NO: 1, particularly at least 90%, 95%, 97%, or 99% homology. In a particular embodiment, the variant of the instant invention has at least 75%, 80%, 85%, 90%, 95%, 97%, 99%, or 100% homology with amino acids 29-461 of SEQ ID NO: 1, particularly at least 90%, 95%, 97%, or 99% homology. In a particular embodiment, the variant of the instant invention has at least 75%, 80%, 85%, 90%, 95%, 97%, 99%, or 100% homology with amino acids 47-461 of SEQ ID NO: 1, particularly at least 90%, 95%, 97%, or 99% homology. In a particular embodiment, the variant comprises a light and heavy chain, wherein the light chain has at least 75%, 80%, 85%, 90%, 95%, 97%, 99%, or 100% homology with SEQ ID NO: 2, particularly at least 90%, 95%, 97%, or 99% homology, and wherein the heavy chain has at least 75%, 80%, 85%, 90%, 95%, 97%, 99%, or 100% homology with SEQ ID NO: 3, particularly at least 90%, 95%, 97%, or 99% homology. In a particular embodiment, the variant comprises a light and heavy chain, wherein the light chain has at least 75%, 80%, 85%, 90%, 95%, 97%, 99%, or 100% homology with SEQ ID NO: 2, particularly at least 90%, 95%, 97%, or 99% homology, and wherein the heavy chain has at least 75%, 80%, 85%, 90%, 95%, 97%, 99%, or 100% homology with SEQ ID NO: 4, particularly at least 90%, 95%, 97%, or 99% homology. The homology percentages above exclude the substitutions at positions 16 and/or 17.

The variants of the instant invention may also be post-translationally modified (γ-carboxylation). The variants may be posttranslationally modified in a cell or in vitro.

In a particular embodiment, the variants of the instant invention have an increased biologic half-life in plasma (e.g., hemophilia plasma). In a particular embodiment, the variants of the invention in the absence of FVIIIa are refractory to all active site function and are poor activators. The variants exhibit enhanced activity in the presence of FVIIIa.

The FIXa variants of the instant invention may comprise at least one substitution at position 16 and/or 17 (by chymotrypsin numbering; positions 227 and 228 in FIG. 2A (SEQ ID NO: 1)). In a particular embodiment, the valine at position 16 is substituted with a non-basic and/or a non-acidic amino acid. In a particular embodiment, the valine at position 16 is substituted with isoleucine, proline, leucine, serine, asparagine, methionine, or threonine. In a particular embodiment, the valine at position 16 is substituted with isoleucine, methionine, leucine, or threonine. In a particular embodiment, the valine at position 16 is substituted with leucine or methionine. In a particular embodiment, the valine at position 16 is substituted with isoleucine or threonine. In a particular embodiment, the valine at position 17 is substituted with a non-acidic amino acid. In a particular embodiment, the valine at position 17 is substituted with isoleucine, asparagine, glutamine, arginine, serine, methionine, or threonine. In a particular embodiment, the valine at position 17 is substituted with isoleucine, glutamine, methionine, or threonine. In a particular embodiment, the valine at position 17 is substituted with isoleucine, threonine, or methionine. The variants of the instant invention may comprise at least one of the above substitutions at position 16 and/or 17. The variants of the instant invention may further comprise at least one other substitution (e.g., at position 18, 19, and/or 194 in chymotrypsin numbering).

Nucleic acid molecules encoding the above variants are also encompassed by the instant invention. Nucleic acid molecules encoding the variants may be prepared by any method known in the art. The nucleic acid molecules may be maintained in any convenient vector, particularly an expression vector.

Compositions comprising at least one variant polypeptide and at least one carrier are also encompassed by the instant invention. Compositions comprising at least one variant nucleic acid molecule and at least one carrier are also encompassed by the instant invention. Except insofar as any conventional carrier is incompatible with the variant to be administered, its use in the pharmaceutical composition is contemplated. In a particular embodiment, the carrier is a pharmaceutically acceptable carrier for intravenous administration.

Definitions

Various terms relating to the biological molecules of the present invention are used hereinabove and also throughout the specification and claims.

The phrase "hemostasis related disorder" refers to bleeding disorders such as, without limitation, hemophilia A, hemophilia B, hemophilia A and B patients with inhibitory antibodies, deficiencies in at least one coagulation factor (e.g., Factors VII, IX, X, XI, V, XII, II, and/or von Willebrand factor, particularly Factor IX), combined FV/FVIII deficiency, vitamin K epoxide reductase C1 deficiency, gamma-carboxylase deficiency; bleeding associated with trauma, injury, thrombosis, thrombocytopenia, stroke, coagulopathy (hypocoagulability), disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency. In a particular embodiment, the hemostasis related disorder is hemophilia B.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to protein, the term "isolated protein" is sometimes used herein. This term may refer to a protein produced by expression of an isolated nucleic acid molecule of the invention. Alternatively, this term may refer to a protein which has been sufficiently separated from other proteins with which it would naturally be associated (e.g., so as to exist in "substantially pure" form).

The term "vector" refers to a carrier nucleic acid molecule (e.g., RNA or DNA) into which a nucleic acid sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight the compound of interest (e.g., nucleic acid, oligonucleotide, protein, etc.), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

Preparation of Variant Encoding Nucleic Acid Molecules and Polypeptides

Nucleic acid molecules encoding the variants of the invention may be prepared by using recombinant DNA technology methods. The availability of nucleotide sequence information enables preparation of isolated nucleic acid molecules of the invention by a variety of means. For example, nucleic acid sequences encoding a variant may be isolated from appropriate biological sources using standard protocols well known in the art.

Nucleic acids of the present invention may be maintained as RNA or DNA in any convenient cloning vector. In a particular embodiment, clones are maintained in a plasmid cloning/expression vector (e.g., pBluescript (Stratagene, La Jolla, Calif.)), which is propagated in a suitable E. coli host cell. Alternatively, the nucleic acids may be maintained in a vector suitable for expression in mammalian cells. In cases where post-translational modification affects variant function, it is preferable to express the molecule in mammalian cells.

In one embodiment, the nucleic acids encoding the variants of the instant invention may be further modified via insertion of an intracellular proteolytic cleavage site (the instant invention also encompasses the resultant polypeptide both before and after cleavage). In order to express FIXa variants in mammalian cells, an intracellular proteolytic cleavage site (e.g., PACE/furin cleavage site) can be inserted between positions $Arg^{15}$ and $Val^{16}$ in the variant Factor IX. Such cleavage sites include, without limitation: Arg-Xaa-(Arg/Lys)-Arg (SEQ ID NO: 7), Arg-Lys-Arg, or Arg-Lys-Arg-Arg-Lys-Arg (SEQ ID NO: 8). These cleavage sites are efficiently recognized by proteases (PACE/furin-like enzymes) within the cell and are removed. This results in a processed variant FIXa in which the heavy chain on the molecule begins at position 16. Introduction of this cleavage site at this position will allow for the intracellular conversion of Factor IX to FIXa. In another embodiment, part or all of the 35 amino acid activation peptide can be removed and the intracellular protease cleavage site can be introduced in its place which will result in FIXa variants upon expression.

Ultimately these types of modifications allow for secretion of the "active" processed form of variant Factor IX from a cell that expresses the modified variant Factor IX. Secretion of the cleaved factor obviates a need for proteolytic cleavage during blood clotting or following the isolation of the protein.

Variant encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting variant expression.

The variants of the present invention may be prepared in a variety of ways, according to known methods. The protein may be purified from appropriate sources (e.g., transformed bacterial or animal cultured cells or tissues which express variants), for example, by immunoaffinity purification. The availability of nucleic acid molecules encoding the variants enables production of the variants using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega or Life Technologies.

Alternatively, larger quantities of variant may be produced by expression in a suitable prokaryotic or eukaryotic expression system. For example, part or all of a DNA molecule encoding the variant may be inserted into a plasmid vector adapted for expression in a bacterial cell, such as E. coli or a mammalian cell such as CHO or HeLa cells. Alternatively, tagged fusion proteins comprising the variant can be generated. Such variant-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as E. coli or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant proteins, produced by gene expression in a recombinant prokaryotic or eukaryotic system may be purified according to methods known in the art. In a particular embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

Variant proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as in reticulocyte lysates.

Uses of Variant Proteins and Variant-Encoding Nucleic Acids

Variant nucleic acids encoding polypeptides having altered protease activities may be used according to this invention, for example, as therapeutic and/or prophylactic agents (protein or nucleic acid) which modulate the blood coagulation cascade. It is demonstrated herein that the variant molecules can increase coagulation and provide effective hemostasis.

In a particular embodiment of the present invention, variant polypeptides may be administered to a patient via infusion in a biologically compatible carrier, preferably via intravenous injection. The variants of the invention may optionally be encapsulated into liposomes or mixed with other phospholipids or micelles to increase stability of the molecule. Variants may be administered alone or in combination with other agents known to modulate hemostasis (e.g., Factor VIII, Factor VIIIa or derivatives thereof). An appropriate composition in which to deliver variant polypeptides may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified variants contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the variant can be stored in the form of a finished solution or in lyophilized or deep-frozen form. In a particular embodiment, the preparation is stored in lyophilized form and is dissolved into a visually clear solution using an appropriate reconstitution solution. Alternatively, the preparation according to the present invention can also be made available as a liquid preparation or as a liquid that is deep-frozen. The preparation according to the present invention is especially stable, i.e., it can be allowed to stand in dissolved form for a prolonged time prior to application.

The preparation according to the present invention which contains a Factor IX variant in combination with Factor VIIa/TF complex or FXIa or a derivative thereof which is able to activate the Factor IX variant into FIXa or the FIXa variant can be made available in the form of a combination preparation comprising a container that holds Factor VIIa/TF complex or FXIa which is immobilized on a matrix, potentially in the form of a miniature column or a syringe complemented with a protease, and a container containing the pharmaceutical preparation with the Factor IX variant. To activate the Factor IX variant, the Factor IX variant-containing solution, for example, can be pressed over the immobilized protease. During storage of the preparation, the Factor IX variant-containing solution is preferably spatially separated from the protease. The preparation according to the present invention can be stored in the same container as the protease, but the components are spatially separated by an impermeable partition which can be easily removed before administration of the preparation. The solutions can also be stored in separate containers and be brought into contact with each other only shortly prior to administration.

The Factor IX variant can be activated into FIXa shortly before immediate use, i.e., prior to the administration to the patient. The activation can be carried out by bringing a Factor IX variant into contact with an immobilized protease or by mixing solutions containing a protease, on the one hand, and the Factor IX variant, on the other hand. Thus, it is possible to separately maintain the two components in solution and to mix them by means of a suitable infusion device in which the components come into contact with each other as they pass through the device and thereby to cause an activation into FIXa or into the FIXa variant. The patient thus receives a mixture of FIXa and, in addition, a serine protease which is responsible for the activation. In this context, it is especially important to pay close attention to the dosage since the additional administration of a serine protease also activates endogenous Factor IX, which may shorten the coagulation time.

The preparation according to the present invention can be made available as a pharmaceutical preparation with FIXa activity in the form of a one-component preparation or in combination with other factors in the form of a multi-component preparation.

Prior to processing the purified protein into a pharmaceutical preparation, the purified protein may be subjected to the conventional quality controls and fashioned into a therapeutic form of presentation. In particular, during the recombinant manufacture, the purified preparation may be tested for the absence of cellular nucleic acids as well as nucleic acids that are derived from the expression vector, particularly using a method, such as is described in EP 0 714 987.

Another feature of this invention relates to making available a preparation which contains a FIXa variant with a high stability and structural integrity and which, in particular, is free from inactive Factor IX/IXa intermediates and autoproteolytic degradation products and which can be produced by activating a Factor IX variant of the type described above and by formulating it into an appropriate preparation.

The pharmaceutical preparation may contain, as an example, dosages of between about 1-1000 µg/kg, about 10-500 µg/kg, about 10-250 µg/kg, or about 10-100 µg/kg. The amounts may be administered intravenously at least one a day. Patients may be treated immediately upon presentation at the clinic with a bleed or prior to the delivery of cut/wound causing a bleed. Alternatively, patients may receive a bolus infusion every one to three hours, or if sufficient improvement is observed, a once daily infusion of the variant described herein.

Variant-encoding nucleic acids may be used for a variety of purposes in accordance with the present invention. In a particular embodiment of the invention, a nucleic acid delivery vehicle (i.e., an expression vector) for modulating blood coagulation is provided wherein the expression vector comprises a nucleic acid sequence coding for a variant polypeptide, or a functional fragment thereof as described herein. Administration of variant-encoding expression vectors to a patient results in the expression of variant polypeptide which serves to alter the coagulation cascade. In accordance with the present invention, a variant encoding nucleic acid sequence may encode a variant polypeptide as described herein whose expression increases hemostasis. In a particular embodiment, the nucleic acid sequence encodes a human FIXa polypeptide variant.

Expression vectors comprising variant nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a particular embodiment of the invention, the expression vector comprising nucleic acid sequences encoding the variant is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-2, AAV-5, AAV-7, and AAV-8) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, and retroviral vectors.

In a particular embodiment of the present invention, methods are provided for the administration of a viral vector comprising nucleic acid sequences encoding a variant or a functional fragment thereof. Adenoviral vectors of utility in the methods of the present invention preferably include at least the essential parts of adenoviral vector DNA. As described herein, expression of a variant polypeptide following administration of such an adenoviral vector serves to modulate hemostasis, particularly to enhance the procoagulation activity of the protease.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for such applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans comprising mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Mitani and Kubo (2002, Curr Gene Ther. 2(2):135-44); Olmsted-Davis et al. (2002, Hum Gene Ther. 13(11):1337-47); Reynolds et al. (2001, Nat Biotechnol. 19(9):838-42); U.S. Pat. No. 5,998,205 (wherein tumor-specific replicating vectors comprising multiple DNA copies are provided); U.S. Pat. No. 6,228,646 (wherein helper-free, totally defective adenovirus vectors are described); U.S. Pat. No. 6,093,699 (wherein vectors and methods for gene therapy are provided); U.S. Pat. No. 6,100,242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant or functional fragments thereof. For example, an E1 deleted type 5 adenoviral vector comprising nucleic acid sequences encoding variant under the control of a cytomegalovirus (CMV) promoter may be used to advantage in the methods of the present invention.

Adenoviral vectors for recombinant gene expression have been produced in the human embryonic kidney cell line 293 (Graham et al., 1977, J. Gen. Virol. 36:59-72). This cell line is permissive for growth of adenovirus 2 (Ad2) and adenovirus 5 mutants defective in E1 functions because it comprises the left end of the adenovirus 5 genome and, therefore, expresses E1 proteins. E1 genes integrated into the cellular genome of 293 cells are expressed at levels which facilitate the use of these cells as an expression system in which to amplify viral vectors from which these genes have been deleted. 293 cells have been used extensively for the isolation and propagation of E1 mutants, for helper-independent cloning, and for expression of adenovirus vectors. Expression systems such as the 293 cell line, therefore, provide essential viral functions in trans and thereby enable propagation of viral vectors in which exogenous nucleic acid sequences have been substituted for E1 genes. See Young et al. in The Adenoviruses, Ginsberg, ed., Plenum Press, New York and London (1984), pp. 125-172. Other expression systems well suited to the propagation of adenoviral vectors are known to those of skill in the art (e.g., HeLa cells) and have been reviewed elsewhere.

Also included in the present invention is a method for modulating hemostasis comprising providing cells of an individual with a nucleic acid delivery vehicle encoding a variant polypeptide and allowing the cells to grow under conditions wherein the variant polypeptide is expressed.

From the foregoing discussion, it can be seen that variant polypeptides, and variant polypeptide expressing nucleic acid vectors may be used in the treatment of disorders associated with aberrant blood coagulation.

The expression vectors of the present invention may be incorporated into pharmaceutical compositions that may be delivered to a subject, so as to allow production of a biologically active protein (e.g., a variant polypeptide or functional fragment or derivative thereof). In a particular embodiment of the present invention, pharmaceutical compositions comprising sufficient genetic material to enable a recipient to produce a therapeutically effective amount of a variant polypeptide can influence hemostasis in the subject. Alternatively, as discussed above, an effective amount of the variant polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In particular embodiments, the pharmaceutical compositions also contain a pharmaceutically acceptable excipient/carrier. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of variant-containing vectors or polypeptides, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant polypeptide. Thus, a therapeutically effective amount in humans will fall in a relatively broad range that may be determined by a medical practitioner based on the response of an individual patient to vector-based variant treatment.

The variant polypeptides, alone or in combination with other agents may be directly infused into a patient in an appropriate biological carrier as described hereinabove. Expression vectors of the present invention comprising nucleic acid sequences encoding variant or functional fragments thereof, may be administered to a patient by a variety of means (see below) to achieve and maintain a prophylactically and/or therapeutically effective level of the variant polypeptide. One of skill in the art could readily determine specific protocols for using the variant encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

Variant encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising variant nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant polypeptide. Also provided are lentiviruses or pseudo-typed lentivirus vectors comprising a nucleic acid sequence encoding a variant polypeptide. Also encompassed are naked plasmid or expression vectors comprising a nucleic acid sequence encoding a variant polypeptide.

The following examples are provided to illustrate various embodiments of the present invention. The examples are illustrative and are not intended to limit the invention in any way.

EXAMPLE 1

A series of recombinant Factor IX derivatives, wherein an amino acid at position 16 or 17 was modified, was tested for activity. Because of the amino acids substitutions at these positions, the transition from zymogen to protease will be altered. Notably, several naturally-occurring mutations at these positions have been identified. Specifically, the substitutions of Val[16] with Phe, Asp, or Ala have been described and substitutions of Val[17] with Leu, Phe, Ala, or Gly have also been described. These naturally occurring variants account for a wide spectrum of clinical severity. Accordingly, a new panel of Factor IX variants was tested. Specifically, Val[16] was substituted with Ile, Pro, Leu, Ser, Asn, Met, or Thr and Val[17] was substituted with Ile, Gln, Arg, Ser, Asn, Met, or Thr. Briefly, HEK 293 cells in 100 mm plates were transiently transfected with plasmids expressing the Factor IX variant. Media from the transfected cells was collected at 48 hours and Factor IX activity was assessed in a one stage Factor IX specific clotting assay. Antigen levels were determined with a Factor IX specific ELISA. Factor IX variant specific activity was normalized to antigen levels to control for experimental variation. As shown in FIG. 1, substitutions at position 16 or 17 yield Factor IX variants with a range of activity, but all significantly less than wild-type. Table 1 provides the antigen levels and activity levels following stable transfection as percent of wild-type. Table 2 provides the activity of certain purified FIX variants compared to wild-type levels. FIX activity levels were based on one stage FIX specific clotting.

TABLE 1

Antigen and activity levels normalized to wild-type FIX antigen and activity levels.

| Construct | % wt-Antigen | % wt-Activity |
|---|---|---|
| Val 16→Ile | 108 | 100 |
| Val 17→Ile | 88 | 83 |
| Val 16→Met | 92 | 9 |
| Val 17→Ser | 87 | 8 |
| Val 17→Thr | 118 | 8 |
| Val 16→Leu | 60 | 6 |
| Val 17→Met | 60 | 4 |
| Val 17→Gln | 75 | 2 |
| Val 17→Asn | 61 | <1 |
| Val 16→Thr | 35 | <1 |
| Val 17→Arg | 54 | <1 |
| Val 16→Asn | 53 | <1 |
| Val 16→Ser | 18 | <1 |
| Val 16→Pro | 69 | <1 |

TABLE 2

Activity levels of purified FIX variants normalized to wild-type FIX activity levels.

| | % wt-Activity (purified proteins) |
|---|---|
| wt-FIX | 100 |
| FIX-V17I | 70 |
| FIX-V16M | 29 |
| FIX-V17T | 19 |
| FIX-V17S | 12 |
| FIX-V16L | 9 |
| FIX-V17M | 4 |
| FIX-V16T (v7) | 1.3 |
| FIX-V16N (v5) | 0.003 |

EXAMPLE 2

Figure 3A:
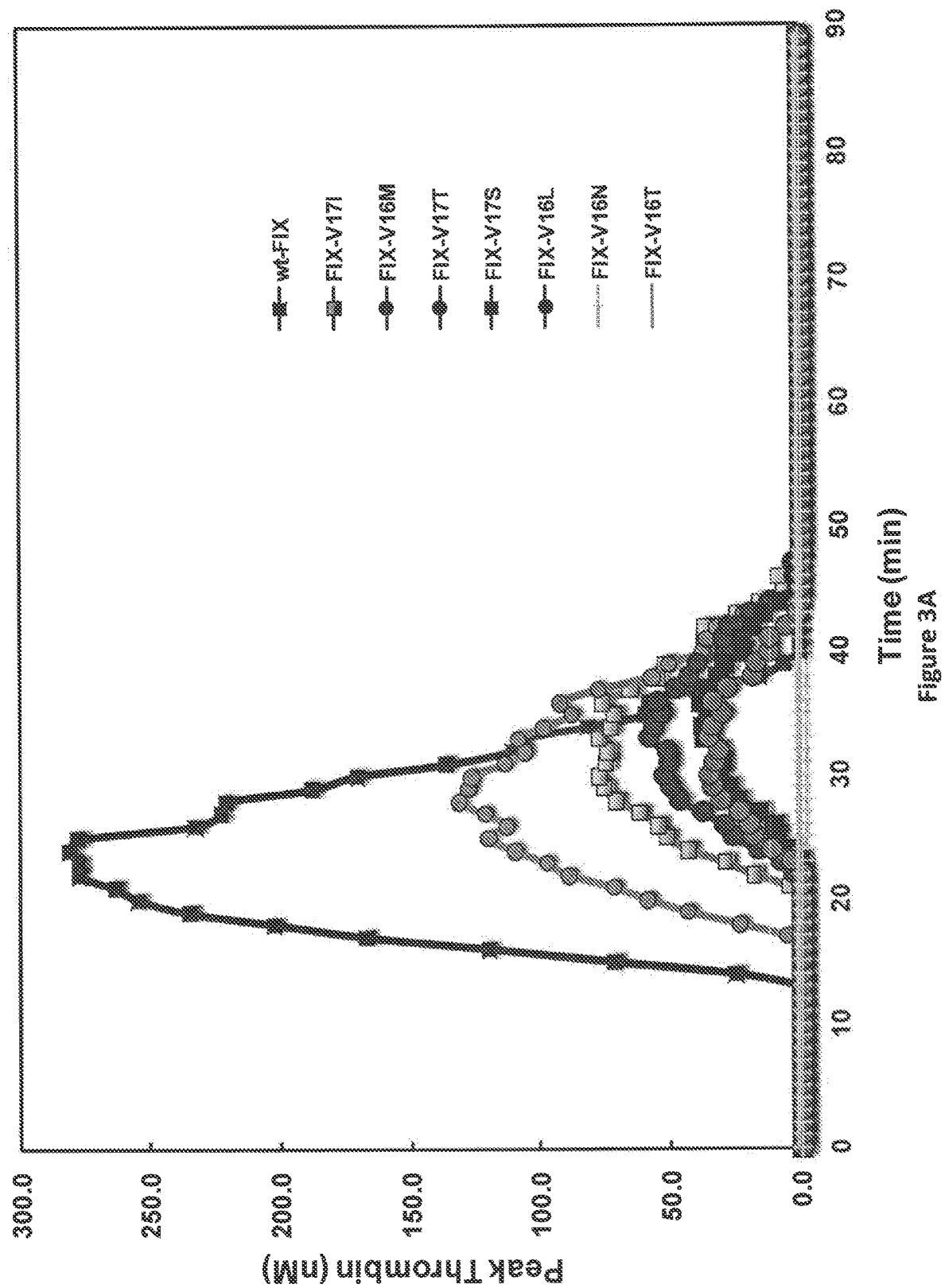
FIG. 3A provides a timecourse of the tissue factor initiated thrombin generation by wild-type FIX and the FIX variants.
Figure 3B:
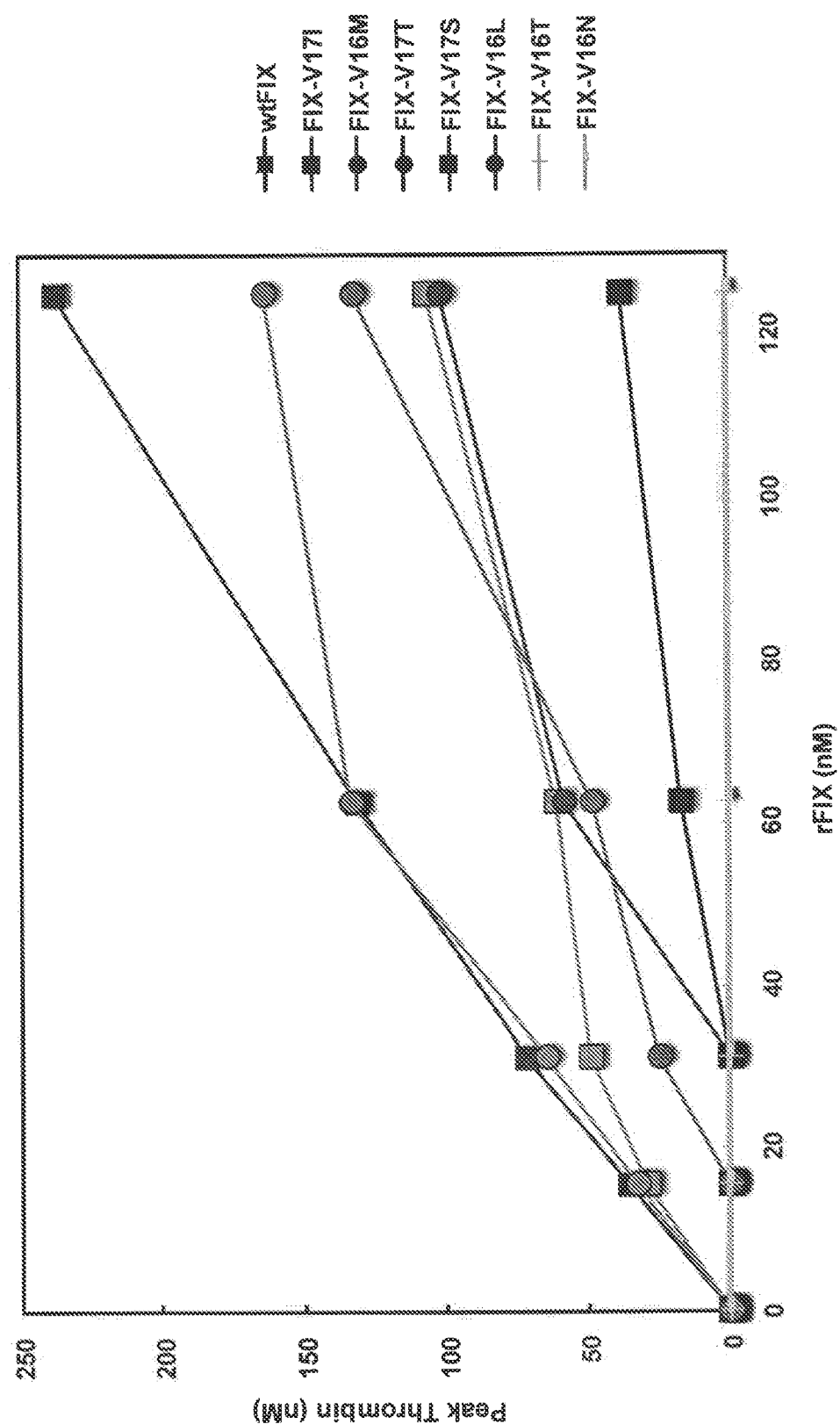
FIG. 3B provides a graph of the peak thrombin for each FIX plotted as a function of the FIX concentration. The data are representative of 2-3 experiments.

Coagulation and thrombin generation activity of the FIX variants were tested. Briefly, an activated partial thromboplastin time (aPTT) assay to determine clotting time was performed where 50 μL of human hemophilia B (HB) plasma was mixed with 50 μL of aPTT reagent followed by a 180-second incubation period at 37° C. A 50 μL mixture of FIX (90-360 nM) in assay buffer was then added to the solution and coagulation was initiated with 50 μL of 25 mM $CaCl_2$. For the thrombin generation assay (TGA), thrombin generation was measured in human HB plasma supplemented with 90 nM of FIX in the presence of 2.0 pM tissue factor/4 μM phospholipids (Technothrombin® TGA reagent B (RB); Technoclone, Vienna, Austria). Thrombin generation was initiated with $CaCl_2$ and a fluorogenic substrate Z-Gly-Gly-Arg-AMC. Table 3 provides the results of the aPTT assay and TGA assay. FIG. 3A provides a timecourse of the tissue factor initiated thrombin generation by wild-type FIX and the FIX variants. FIG. 3B provides a graph of the peak thrombin for each FIX plotted as a function of the FIX concentration.

TABLE 3

Results of the aPTT and TGA assays.

| | aPTT assay Clotting time (sec) | | | Thrombin generation assay (TGA) | | |
|---|---|---|---|---|---|---|
| | | | | Peak of thrombin (nM) | ETP nm min | Lag time (min) |
| | 90 nM | 180 nM | 360 nM | 90 nM FIX | | |
| wt-FIX | 41 | 38 | 36.6 | 281 | 4100 | 14 |
| FIX-V17I | 45 | 41.6 | — | 77 | 1260 | 19 |
| FIX-V16M | 49 | 48 | 47 | 131 | 2171 | 16 |
| FIX-V17T | 56 | 54 | 52 | 58 | 846 | 20 |
| FIX-V17S | 57.5 | 54 | 54 | 38 | 513 | 22 |
| FIX-V16L | 59 | 56 | 53 | 43 | 597 | 19 |
| FIX-V16T | 77.5 | 74 | 74 | 0 | 0 | 31 |
| FIX-V16N | 127.6 | — | — | 0 | 0 | 28 |

ETP = endogenous thrombin potential.

Figure 4A:
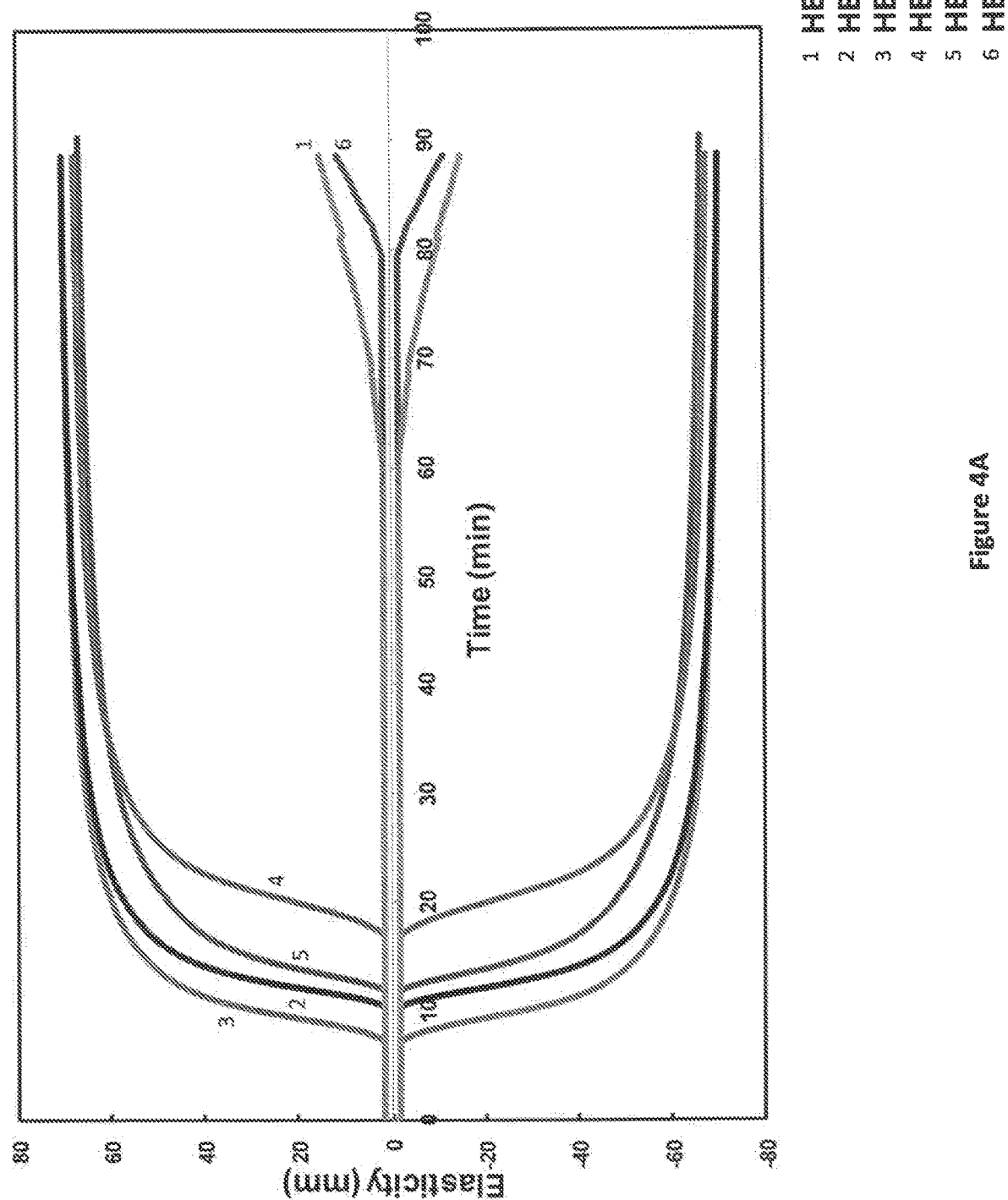
FIG. 4A provides a graph of rotational thromboelastograms performed using freshly collected whole blood from hemophilia mice after injection with phosphate buffered saline (PBS), wild-type FIX, or the indicated FIX variant (250 µg/kg).

To assay these FIX in whole blood, rotational thromboelastography (ROTEM) experiments were performed using the FIX. In ROTEM, a rotating pin is submerged in a cup containing whole blood. A coagulation initiator is added, and as the blood clots, rotation of the pin is restricted, which is detected optically by the instrument. In these experiments, HB mice were injected with FIX (250 μg/kg; n=2-3/group) and the whole blood was collected 5 minutes after injection. As shown in FIG. 4A, FIX V17I, FIX V16M, and V16L approached or surpassed normal clot times by wild-type FIX.

Figure 4B:
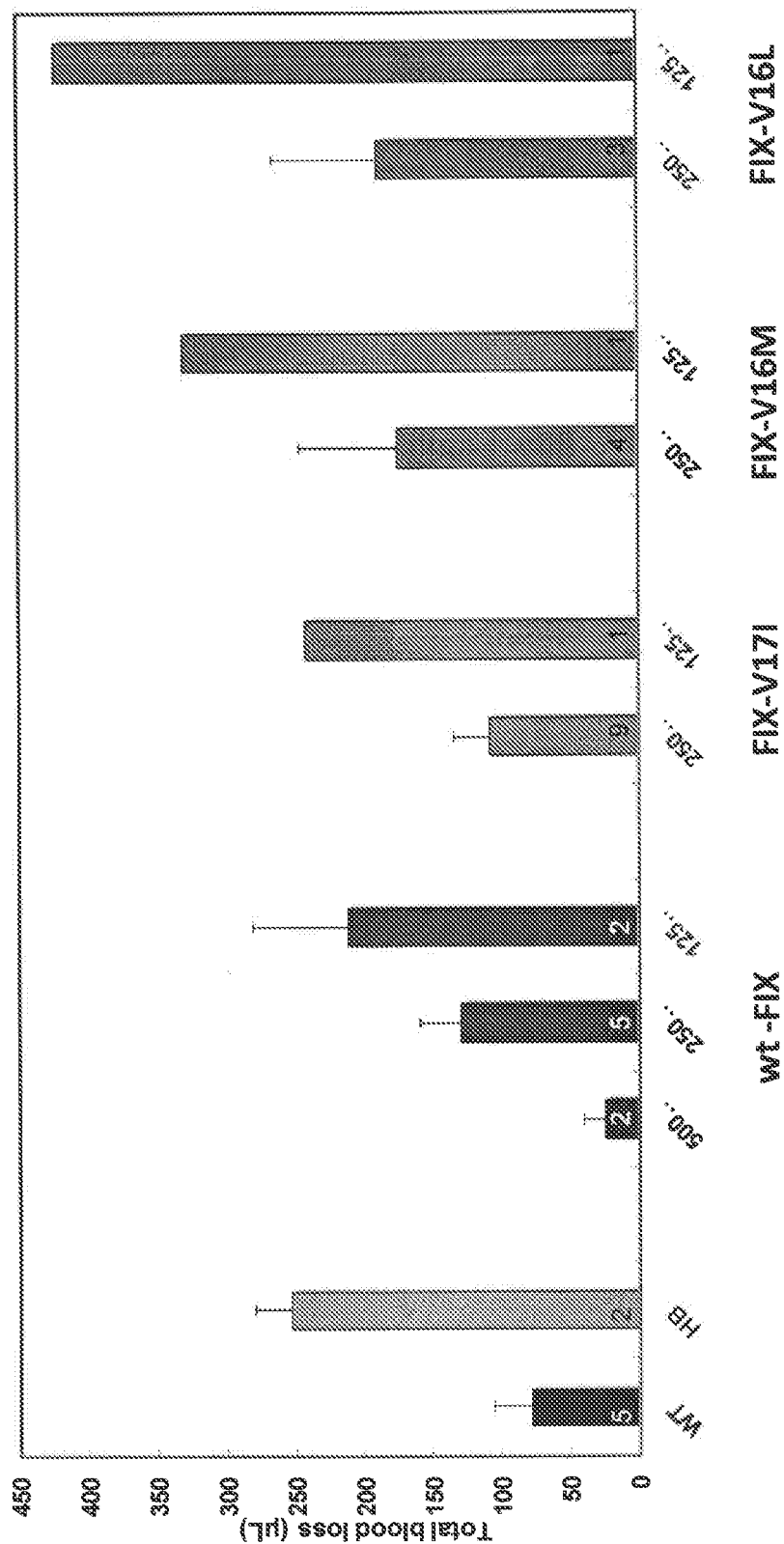
FIG. 4B provides a graph total blood loss following tail clip of FIX treated HB mice. Five minutes prior to the tail clip injury, wt-FIX or FIX variants was administered to HB (Balb/c) mice via tail vein at the indicated dosage (125 µg/kg, 250 µg/kg, or 500 µg/kg). Wild-type mice (WT) and hemophilia B mice (HB) injected with PBS were used as controls. Total blood loss (µL) was then measured for 10 minutes following tail transection. The number of animals is indicated and measurements are presented as ±SEM.

FIG. 4B provides a graph total blood loss following tail clip of FIX treated HB mice. Briefly, five minutes prior to the tail clip injury, wt-FIX or FIX variants was administered to HB (Balb/c) mice via tail vein at the indicated dosage (125 μg/kg, 250 μg/kg, or 500 μg/kg). Wild-type mice (WT) and hemophilia B mice (HB) injected with PBS were used as controls. Total blood loss (μL) was then measured for 10 minutes following tail transection. The number of animals is indicated and measurements are presented as ±SEM. While all of the FIX variants exhibited decreasing blood loss with increasing concentrations of FIX, FIX V17I exhibited clotting times similar to or better than wild-type FIX.

EXAMPLE 3

Activated FIX variants (FIXa) were also studied. First, the ex vivo half-life ($t_{1/2}$) of the FIXa variants was determined in HB plasma. Briefly, 100 nM wt-FIXa or FIXa variants were incubated in human HB plasma at room temperature and at various time points aliquots of the reaction were further diluted (1-3 nM FIXa, final) in 20 mM Hepes, 0.15 M NaCl, 0.1% polyethylene glycol 8000, pH 7.5 (dilution buffer). Residual FIXa coagulant activity was assessed using an aPTT assay. For the thrombin generation assay, FIXa-initiated thrombin generation was assayed in human HB plasma supplemented with 25 pM wt-FIXa or FIXa variants in the presence of 4 µM of phospholipid vesicles (PCPS) vesicles. Table 4 provides the results showing that FIXa-V17I most closely mimicked wild-type FIXa while FIX-V16L and FIXa-V16T had very long half-lives.

TABLE 4

Ex vivo half-life ($t_{1/2}$) in HB plasma of wild-type FIXa and FIXa variants. Results of the aPTT assay with wild-type FIXa and FIXa variants are also provided.

|  | $t_{1/2}$ (min) | Peak of IIa (nM) | ETP | Lag time (min) |
| --- | --- | --- | --- | --- |
| wt-FIXa | 39.08 ± 3 | 931 | 6420 | 14 |
| FIXa-V17I | 36.5 ± 1.65 | 568 | 5538 | 14.5 |

TABLE 4-continued

Ex vivo half-life ($t_{1/2}$) in HB plasma of wild-type FIXa and FIXa variants. Results of the aPTT assay with wild-type FIXa and FIXa variants are also provided.

|  | $t_{1/2}$ (min) | Peak of IIa (nM) | ETP | Lag time (min) |
| --- | --- | --- | --- | --- |
| FIXa-V16L | 221.99 ± 23.75 | 397 | 4558 | 23 |
| FIXa-V16T | 655.31 ± 121.21 | 0 | 0 | 0 |

ETP = endogenous thrombin potential.

Figure 5A:
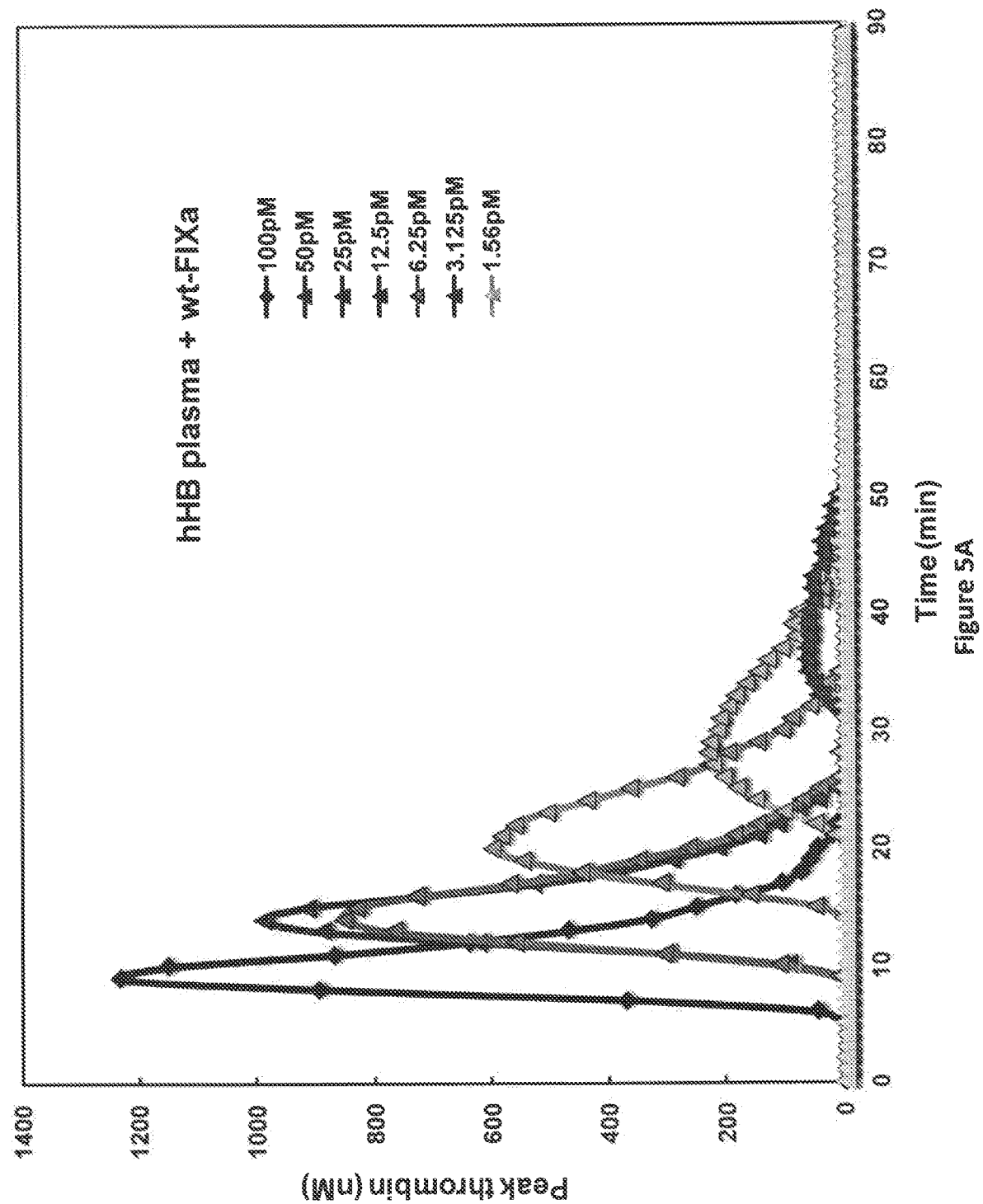
Figure 5B:
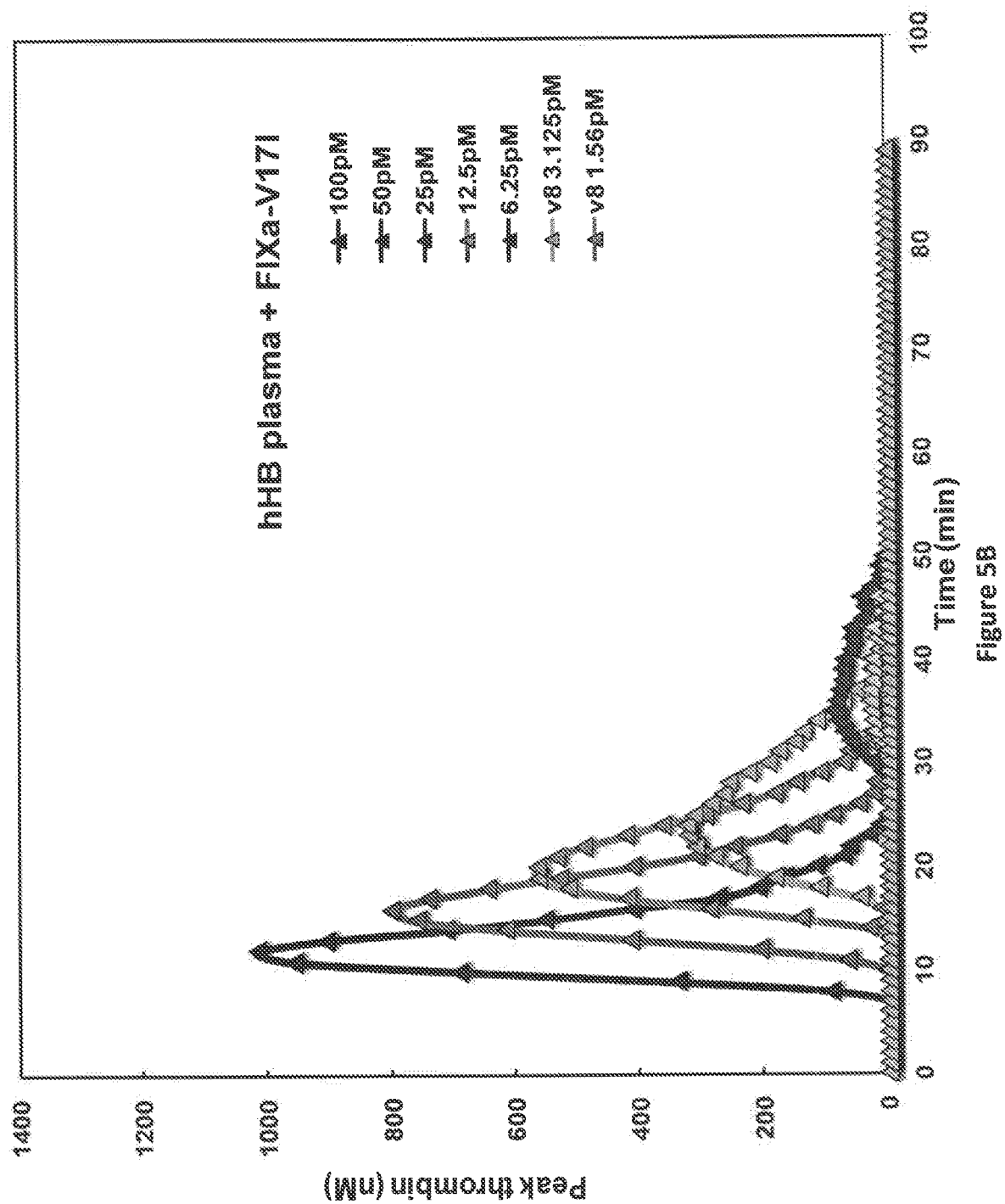
Figure 5D:
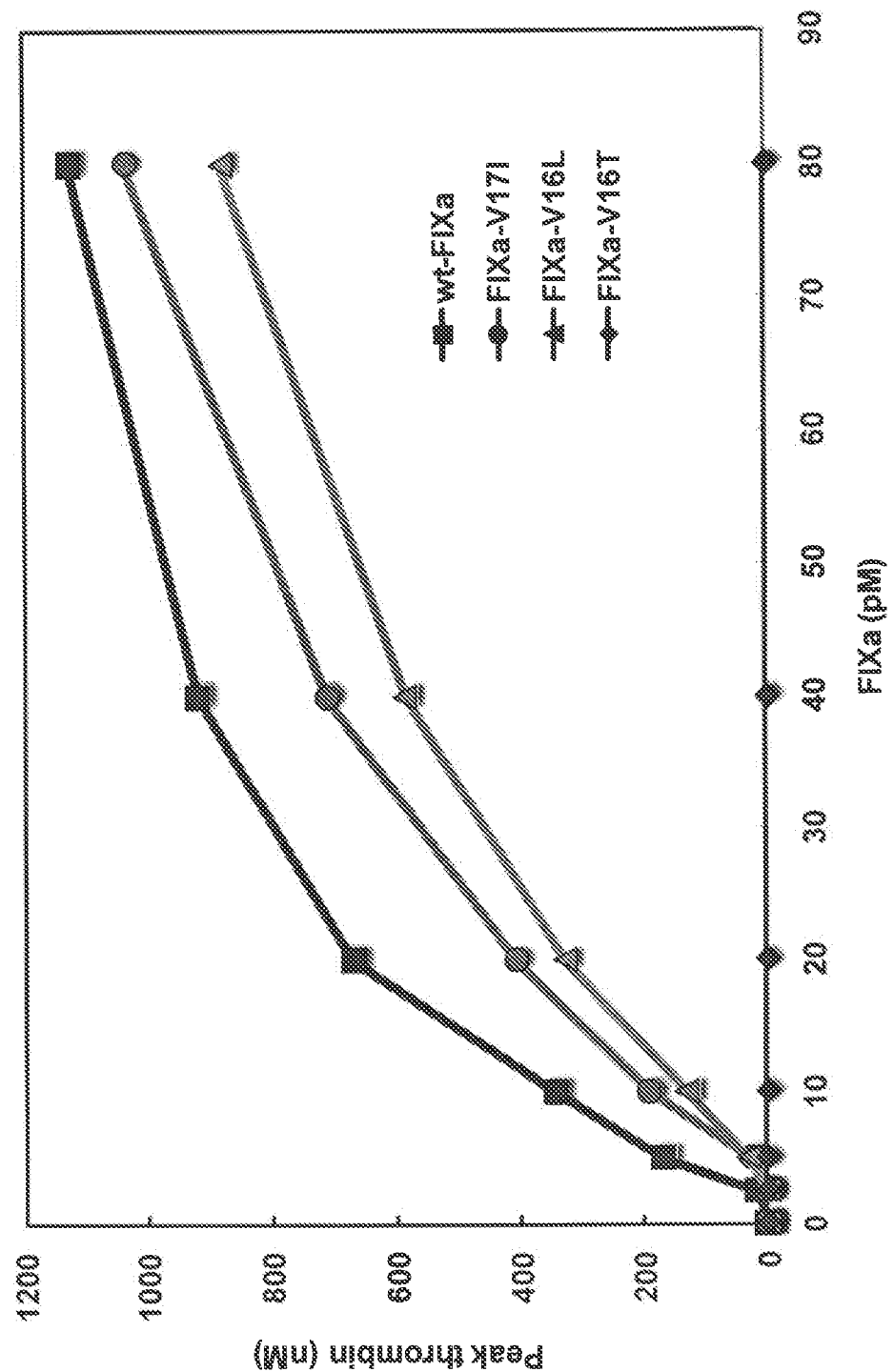
FIG. 5D provides a graph of the peak thrombin for each FIXa plotted as a function of the FIXa concentration. The data are representative of 2-3 similar experiments.

FIGS. 5A, 5B, and 5C provide a timecourse of FIXa thrombin generation for wild-type FIXa, FIXa V17I, and FIXa V16L. FIG. 5D provides a graph of the peak thrombin for each FIXa plotted as a function of the FIXa concentration. FIXa-initiated thrombin generation in human HB plasma was performed in the absence of tissue factor. Briefly, thrombin generation was initiated by 1 to 100 pM of recombinant wt-FIXa or FIXa variant in the presence of 4 µM of PCPS vesicles in HB plasma. Peak of thrombin for each protease is plotted as a function of the protease concentration. The data are representative of 2-3 similar experiments.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A Factor IXa variant which modulates hemostasis, wherein said Factor IXa variant comprises a light and heavy chain, wherein the light chain comprises SEQ ID NO: 2, wherein the heavy chain comprises SEQ ID NO: 4, and wherein said Factor IXa comprises at least one substitution selected from the group consisting of:
   a) the Val at position 1 of SEQ ID NO: 4 is substituted with lie, Pro, Leu, Ser, Asn, Met, or Thr, and
   b) the Val at position 2 of SEQ ID NO: 4 is substituted with lie, Gin, Arg, Ser, Asn, Met, or Thr.

2. The Factor IXa variant of claim 1, wherein the Val at position 1 of SEQ ID NO: 4 is substituted with Leu, Met, Ile or Thr.

3. The Factor IXa variant of claim 1, wherein the Val at position 2 of SEQ ID NO: 4 is substituted with Ille, Thr or Met.

4. The Factor IXa variant of claim 1, comprising a substitution at both positions 1 and 2 of SEQ ID NO: 4.

5. The Factor IXa variant of claim 1, wherein the Factor IXa variant has a longer plasma biologic half life than wild-type Factor IXa.

6. A composition comprising the Factor IXa variant of claim 1 and at least one pharmaceutically acceptable carrier.

* * * * *

SEQUENCE LISTING

<160> NUMBER OF SEQ ID NOS: 8

<210> SEQ ID NO 1
<211> LENGTH: 461
<212> TYPE: PRT
<213> ORGANISM: Homo sapiens

<400> SEQUENCE: 1

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

```
Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
            245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
            370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
            450                 455                 460

<210> SEQ ID NO 2
<211> LENGTH: 145
<212> TYPE: PRT
<213> ORGANISM: Homo sapiens

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
            50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
```

```
                        85                  90                  95

Gln Phe Cys Lys Asn Ser Ala Asp Asn Lys Val Val Cys Ser Cys Thr
                100                 105                 110

Glu Gly Tyr Arg Leu Ala Glu Asn Gln Lys Ser Cys Glu Pro Ala Val
                115                 120                 125

Pro Phe Pro Cys Gly Arg Val Ser Val Ser Gln Thr Ser Lys Leu Thr
            130                 135                 140

Arg
145

<210> SEQ ID NO 3
<211> LENGTH: 270
<212> TYPE: PRT
<213> ORGANISM: Homo sapiens

<400> SEQUENCE: 3

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
                20                  25                  30

Phe Thr Arg Val Val Gly Gly Glu Asp Ala Lys Pro Gly Gln Phe Pro
            35                  40                  45

Trp Gln Val Val Leu Asn Gly Lys Val Asp Ala Phe Cys Gly Gly Ser
    50                  55                  60

Ile Val Asn Glu Lys Trp Ile Val Thr Ala Ala His Cys Val Glu Thr
65                  70                  75                  80

Gly Val Lys Ile Thr Val Val Ala Gly Glu His Asn Ile Glu Glu Thr
                85                  90                  95

Glu His Thr Glu Gln Lys Arg Asn Val Ile Arg Ile Ile Pro His His
                100                 105                 110

Asn Tyr Asn Ala Ala Ile Asn Lys Tyr Asn His Asp Ile Ala Leu Leu
            115                 120                 125

Glu Leu Asp Glu Pro Leu Val Leu Asn Ser Tyr Val Thr Pro Ile Cys
    130                 135                 140

Ile Ala Asp Lys Glu Tyr Thr Asn Ile Phe Leu Lys Phe Gly Ser Gly
145                 150                 155                 160

Tyr Val Ser Gly Trp Gly Arg Val Phe His Lys Gly Arg Ser Ala Leu
                165                 170                 175

Val Leu Gln Tyr Leu Arg Val Pro Leu Val Asp Arg Ala Thr Cys Leu
            180                 185                 190

Arg Ser Thr Lys Phe Thr Ile Tyr Asn Asn Met Phe Cys Ala Gly Phe
    195                 200                 205

His Glu Gly Gly Arg Asp Ser Cys Gln Gly Asp Ser Gly Gly Pro His
            210                 215                 220

Val Thr Glu Val Glu Gly Thr Ser Phe Leu Thr Gly Ile Ile Ser Trp
225                 230                 235                 240

Gly Glu Glu Cys Ala Met Lys Gly Lys Tyr Gly Ile Tyr Thr Lys Val
                245                 250                 255

Ser Arg Tyr Val Asn Trp Ile Lys Glu Lys Thr Lys Leu Thr
            260                 265                 270

<210> SEQ ID NO 4
<211> LENGTH: 235
<212> TYPE: PRT
<213> ORGANISM: Homo sapiens
```

<400> SEQUENCE: 4

```
Val Val Gly Gly Glu Asp Ala Lys Pro Gly Gln Phe Pro Trp Gln Val
1               5                   10                  15
Val Leu Asn Gly Lys Val Asp Ala Phe Cys Gly Gly Ser Ile Val Asn
            20                  25                  30
Glu Lys Trp Ile Val Thr Ala Ala His Cys Val Glu Thr Gly Val Lys
        35                  40                  45
Ile Thr Val Val Ala Gly Glu His Asn Ile Glu Thr Glu His Thr
    50                  55                  60
Glu Gln Lys Arg Asn Val Ile Arg Ile Ile Pro His His Asn Tyr Asn
65                  70                  75                  80
Ala Ala Ile Asn Lys Tyr Asn His Asp Ile Ala Leu Leu Glu Leu Asp
                85                  90                  95
Glu Pro Leu Val Leu Asn Ser Tyr Val Thr Pro Ile Cys Ile Ala Asp
            100                 105                 110
Lys Glu Tyr Thr Asn Ile Phe Leu Lys Phe Gly Ser Gly Tyr Val Ser
        115                 120                 125
Gly Trp Gly Arg Val Phe His Lys Gly Arg Ser Ala Leu Val Leu Gln
    130                 135                 140
Tyr Leu Arg Val Pro Leu Val Asp Arg Ala Thr Cys Leu Arg Ser Thr
145                 150                 155                 160
Lys Phe Thr Ile Tyr Asn Asn Met Phe Cys Ala Gly Phe His Glu Gly
                165                 170                 175
Gly Arg Asp Ser Cys Gln Gly Asp Ser Gly Gly Pro His Val Thr Glu
            180                 185                 190
Val Glu Gly Thr Ser Phe Leu Thr Gly Ile Ile Ser Trp Gly Glu Glu
        195                 200                 205
Cys Ala Met Lys Gly Lys Tyr Gly Ile Tyr Thr Lys Val Ser Arg Tyr
    210                 215                 220
Val Asn Trp Ile Lys Glu Lys Thr Lys Leu Thr
225                 230                 235
```

<210> SEQ ID NO 5
<211> LENGTH: 1386
<212> TYPE: DNA
<213> ORGANISM: Homo sapiens

<400> SEQUENCE: 5

```
atgcagcgcg tgaacatgat catggcagaa tcaccaggcc tcatcaccat ctgccttta       60
ggatatctac tcagtgctga atgtacagtt tttcttgatc atgaaaacgc aacaaaatt      120
ctgaatcggc aaagaggta taattcaggt aaattggaag agtttgttca agggaacctt      180
gagagagaat gtatggaaga aaagtgtagt tttgaagaag cacgaaagt ttttgaaaac      240
actgaaagaa caactgaatt ttggaagcag tatgttgatg agatcagtg tgagtccaat      300
ccatgtttaa atggcggcag ttgcaaggat gacattaatt cctatgaatg ttggtgtccc      360
tttggatttg aaggaaagaa ctgtgaatta gatgtaacat gtaacattaa gaatggcaga      420
tgcgagcagt tttgtaaaaa tagtgctgat aacaaggtgg tttgctcctg tactgaggga      480
tatcgacttg cagaaaacca gaagtcctgt gaaccagcag tgccattcc atgtggaaga      540
gtttctgttt cacaaacttc taagctcacc cgtgctgaga ctgttttcc tgatgtggac      600
tatgtaaatt ctactgaagc tgaaaccatt ttggataaca tcactcaaag cacccaatca      660
tttaatgact tcactcgggt tgttggtgga aagatgcca aaccaggtca attcccttgg      720
```

```
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac cccatgttac tgaagtggaa   1260
gggaccagtt tcttaactgg aattattagc tggggtgaag agtgtgcaat gaaaggcaaa   1320
tatggaatat ataccaaggt atcccggtat gtcaactgga ttaaggaaaa aacaaagctc   1380
acttaa                                                              1386
```

<210> SEQ ID NO 6
<211> LENGTH: 4
<212> TYPE: PRT
<213> ORGANISM: Artificial Sequence
<220> FEATURE:
<223> OTHER INFORMATION: amino terminal sequence

<400> SEQUENCE: 6

Val Val Gly Gly
1

<210> SEQ ID NO 7
<211> LENGTH: 4
<212> TYPE: PRT
<213> ORGANISM: Artificial Sequence
<220> FEATURE:
<223> OTHER INFORMATION: cleavage sequence
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Arg or Lys

<400> SEQUENCE: 7

Arg Xaa Xaa Arg
1

<210> SEQ ID NO 8
<211> LENGTH: 6
<212> TYPE: PRT
<213> ORGANISM: Artificial Sequence
<220> FEATURE:
<223> OTHER INFORMATION: cleavage sequence

<400> SEQUENCE: 8

Arg Lys Arg Arg Lys Arg
1               5